(12) United States Patent
Feinstein et al.

(10) Patent No.: US 6,518,472 B1
(45) Date of Patent: Feb. 11, 2003

(54) STABILIZED DUAL BED XYLENE ISOMERIZATION CATALYST SYSTEM

(75) Inventors: Allen I. Feinstein, Wheaton, IL (US); Ruth Ann Doyle, Naperville, IL (US); Calvin T. Chew, Warrenville, IL (US)

(73) Assignee: BP Corporation North America Inc., Chicago, IL (US)

( * ) Notice: Subject to any disclaimer, the term of this patent is extended or adjusted under 35 U.S.C. 154(b) by 839 days.

(21) Appl. No.: 08/867,511

(22) Filed: Jun. 2, 1997

Related U.S. Application Data
(60) Provisional application No. 60/023,024, filed on Aug. 5, 1996.

(51) Int. Cl.⁷ ................................................ C07C 5/22
(52) U.S. Cl. ..................... 585/477; 585/480; 585/481; 585/482
(58) Field of Search ................................. 585/477, 480, 585/481, 482

(56) References Cited

U.S. PATENT DOCUMENTS

| | | | |
|---|---|---|---|
| 3,702,886 A | 11/1972 | Argauer et al. | 423/328 |
| 3,709,979 A | 1/1973 | Chu | 423/328 |
| 3,729,523 A | 4/1973 | Grandio, Jr. et al. | 260/674 A |
| 3,832,449 A | 8/1974 | Rosinski et al. | 423/328 |
| 3,856,871 A | 12/1974 | Haag et al. | 260/668 A |
| 3,856,874 A | 12/1974 | Hayward | 260/668 A |
| 4,016,245 A | 4/1977 | Plank et al. | 423/328 |
| 4,046,859 A | 9/1977 | Plank et al. | 423/328 |
| 4,098,836 A | 7/1978 | Dywer | 260/668 A |
| 4,101,598 A | 7/1978 | Mitchell et al. | 260/668 A |
| 4,159,283 A | 6/1979 | Nicoletti et al. | 585/481 |
| 4,188,282 A | 2/1980 | Tabak et al. | 208/134 |
| 4,224,141 A | 9/1980 | Morrison et al. | 208/134 |
| 4,268,420 A | 5/1981 | Klotz | 252/432 |
| 4,385,195 A | 5/1983 | Butter et al. | 585/481 |
| 4,420,467 A | 12/1983 | Whittam | 423/328 |
| 4,427,577 A | 1/1984 | Koetsier | 502/66 |
| 4,450,312 A | 5/1984 | Lake et al. | 585/481 |
| 4,467,129 A | 8/1984 | Iwayama et al. | 585/481 |
| 4,482,773 A | 11/1984 | Chu et al. | 585/481 |
| 4,482,774 A | 11/1984 | Koetsier | 585/481 |
| RE31,782 E | 12/1984 | Olson et al. | 585/481 |
| 4,577,048 A | 3/1986 | Chang et al. | 585/467 |
| 4,665,255 A | 5/1987 | Chang et al. | 585/467 |
| 4,697,039 A | 9/1987 | Schmidt | 585/477 |
| 4,725,570 A | 2/1988 | Sikkenga et al. | 502/204 |
| 4,783,568 A | 11/1988 | Schmidt | 585/477 |
| 4,783,571 A | 11/1988 | Chang et al. | 585/481 |
| 4,885,427 A | 12/1989 | Reichmann | 585/480 |
| 4,899,010 A | 2/1990 | Amelse et al. | 585/480 |
| 4,899,011 A | 2/1990 | Chu et al. | 585/481 |
| 5,015,794 A | 5/1991 | Reichmann | 585/258 |
| 5,028,573 A | 7/1991 | Brown et al. | 502/66 |
| 5,053,211 A | 10/1991 | Haddad | 423/277 |

FOREIGN PATENT DOCUMENTS

| | | | |
|---|---|---|---|
| EP | 0006700 | 1/1980 | C07C/5/22 |
| EP | 0234684 | 9/1987 | C07C/5/27 |

OTHER PUBLICATIONS

Meier, W. M., "Zolite Structures", Proceedings of the Conference on Molecular Sieves, London, Apr. 1968, pp. 10–27, published by the Society of Chemical Industry, London 1968.

*Primary Examiner*—Walter D. Griffin
(74) *Attorney, Agent, or Firm*—Mary Jo Kanady

(57) ABSTRACT

A catalyst system suitable for the isomerization of a xylene and conversion of ethylbenzene in a feed containing xylene and ethylbenzene comprising a first catalyst having activity for the conversion of ethylbenzene, a second catalyst having hydrogenation activity and a third catalyst having activity for the isomerization of a xylene where the second catalyst is located in the system between the first and third catalysts relative to a flow of feed material through the catalyst system.

20 Claims, 1 Drawing Sheet

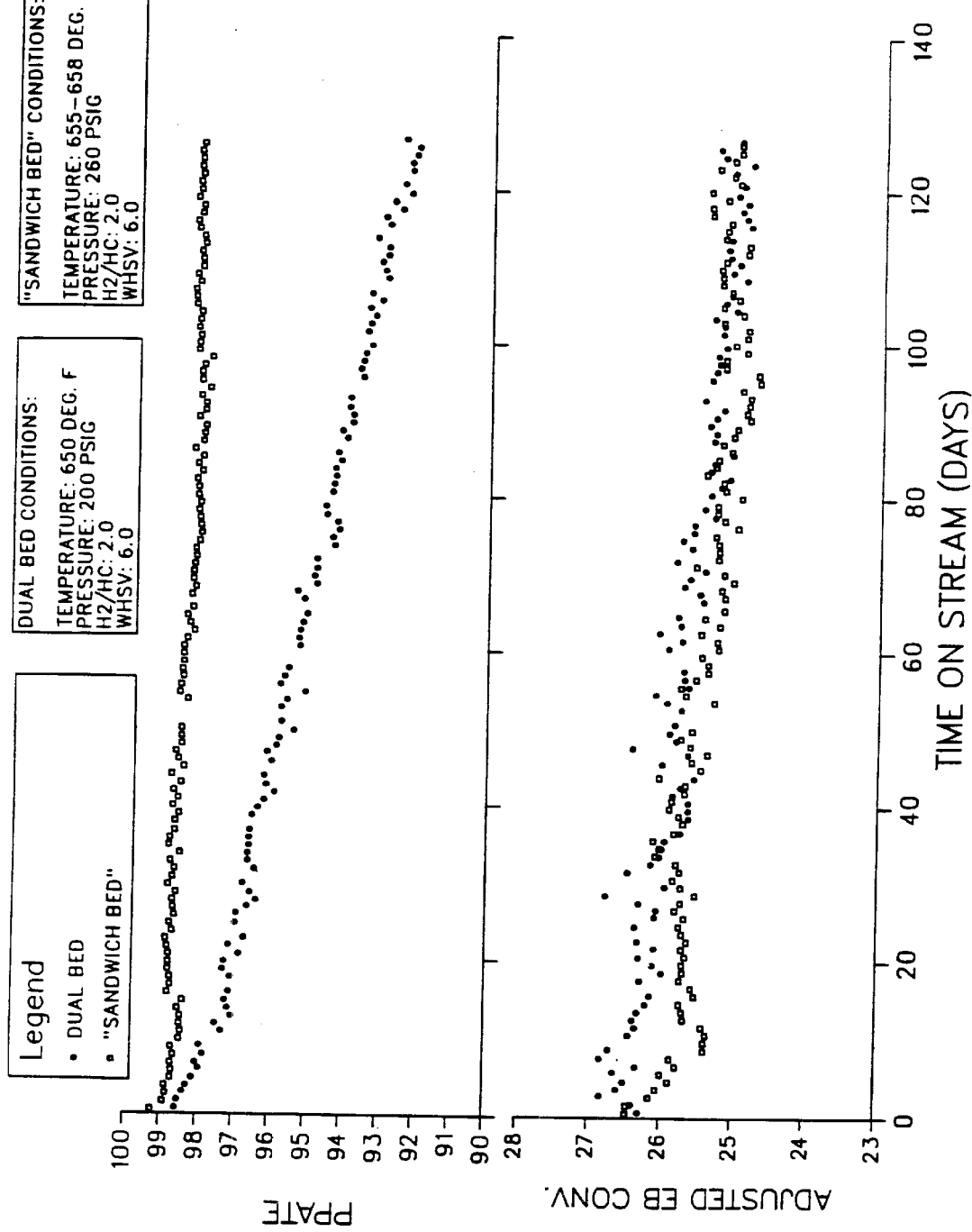
Figure 1. Performance of the Dual Bed vs. "Sandwich Bed"

STABILIZED DUAL BED XYLENE ISOMERIZATION CATALYST SYSTEM

This application claims the benefit of U.S. Provisional Application No. 60/023,024 filed Aug. 5, 1996, which is incorporated herein by reference in its entirety.

FIELD OF THE INVENTION

This invention relates to novel means for stabilizing the xylene isomerization activity of a dual bed xylene isomerization catalyst system. This invention is useful for isomerizing a feed containing an aromatic $C_8$ mixture of xylenes and ethylbenzene (EB) in which the para-xylene content of the xylene-containing portion of the feed is less than the equilibrium content, to produce a product stream of reduced ethylbenzene content and a greater amount of desired para xylene. Para-xylene is an important hydrocarbon feed material for the manufacture of terephthalic acid. The present invention comprises placing a hydrogenation catalyst bed, for example, a molybdenum-on-alumina (Mo/alumina) catalyst bed, between ethylbenzene conversion and xylene isomerization catalyst components to provide an improved catalyst system in which deactivation of the xylene isomerization catalyst component occurs less rapidly.

BACKGROUND OF THE INVENTION

As commercial use of xylenes has increased, there has been continuing interest in methods to isomerize the xylene isomers obtained from processing aromatic naphthas toward an equilibrium mix to increase yields of the more desirable para-xylene. Para-xylene is useful in the manufacture of terephthalic acid which is an intermediate in the manufacture of polyesters. Typically para-xylene is derived from mixtures of $C_8$ aromatics separated from such raw materials as petroleum naphthas, particularly reformates, usually by distillation. The $C_8$ aromatics in such mixtures are ethylbenzene, para-xylene, meta-xylene, and ortho-xylene.

A dual bed catalyst system for converting ethylbenzene and non-aromatics in mixed ethylbenzene xylene containing feeds, while simultaneously converting xylenes to thermal equilibrium is disclosed in U.S. Pat. No. 4,899,011.

A dual bed xylene isomerization catalyst consists of an EB conversion catalyst component and a xylene isomerization component. Typically, the EB conversion catalyst is selective for converting EB to products which can be separated via distillation, while being an ineffective xylene isomerization catalyst, that is, it does not produce an equilibrium distribution of xylene isomers. Such a catalyst system is described in U.S. Pat. No. Re 31,782. This catalyst system has an advantage over a conventional single bed xylene isomerization catalyst in that it affords lower xylene losses. However, catalysts such as those described in U.S. Pat. No. Re 31,782 give unacceptably high deactivation rates. The rapid deactivation of the xylene isomerization catalyst component is believed to be caused by the ethylene that is generated over the EB conversion catalyst. In experiments using only the EB conversion catalyst, we found that the $C_2$ component in the gaseous component of the product consists of more than 80% ethylene.

We solved this deactivation problem by placing a hydrogenation catalyst bed between the EB conversion catalyst component and the xylene isomerization catalyst, referred to herein as a "sandwich" bed. In an experiment with the EB conversion catalyst and a hydrogenation catalyst bed in the form of a Mo/alumina catalyst bed below it, we demonstrated that the ethylene produced over the EB conversion catalyst was quantitatively hydrogenated to ethane without any detrimental effect to the other components in the product.

DESCRIPTION OF THE DRAWINGS

FIG. 1 is a graph showing a comparison of the performance of a dual bed catalyst system and the sandwich bed catalyst system of the present invention.

SUMMARY OF THE INVENTION

The present invention relates to a catalyst system suitable for the isomerization of xylene and conversion of ethylbenzene in a feed containing xylene and ethylbenzene comprising a first catalyst having activity for the conversion of ethylbenzene, a second catalyst having hydrogenation activity and a third catalyst having activity for the isomerization of xylene where the second catalyst is located in the system between the first and third catalysts relative to a flow of feed material through the catalyst system.

The present invention also relates to a method for converting a feed mixture comprising an aromatic $C_8$ mixture of xylenes and ethylbenzene in which the para-xylene content of the xylene portion of the feed is less than equilibrium to produce a product mixture of reduced ethylbenzene content and a greater amount of para-xylene, which method comprises contacting the feed mixture at conversion conditions with a first catalyst having activity for the conversion of ethylbenzene, with a second catalyst having hydrogenation activity, and with a third catalyst having activity for the isomerization of a xylene, wherein the second catalyst is positioned between the first and third catalysts relative to the flow of the feed mixture through the catalysts.

The present invention provides a three component catalyst system for isomerizing a feed containing an aromatic $C_8$ mixture of ethylbenzene and xylene in which the para-xylene is less than at thermal equilibrium which comprises a first catalyst having activity for the conversion of ethylbenzene, a second catalyst having hydrogenation activity and a third catalyst having activity for the isomerization of a xylene and wherein the second catalyst is located in the system between the first and third catalysts relative to a flow of the ethylbenzene/xylene feed through the catalyst system.

The present invention includes a process for isomerizing a feed containing an aromatic $C_8$ mixture of ethylbenzene and xylene in which the para-xylene is less than at thermal equilibrium which comprises contacting the feed under isomerization conditions with a three component catalyst system including component (1), component (2), and component (3) wherein component (1) comprises a catalyst having activity for the conversion of ethylbenzene, component (2) comprises a catalyst having hydrogenation activity, and component (3) comprises a catalyst having activity for the isomerization of a xylene and wherein the component (2) is located in the system between component (1) and component (3) relative to a flow of the ethylbenzene/xylene feed through the catalyst system.

Preferably, the first catalyst having activity for the conversion of ethylbenzene is, an acidic molecular sieve which is characterized by a constraint index in the approximate range of about 1 to about 12, more preferably it is a zeolite, preferably a crystalline aluminosilicate zeolite having a particle size of at least about 1 micron. In one embodiment of the invention, the EB conversion catalyst may contain a hydrogenation metal selected from metals of groups VI and VIII of the Periodic Table of Elements.

Preferably the second catalyst having hydrogenation activity comprises a hydrogenation metal dispersed on a suitable matrix such as alumina or silica. A preferred catalyst is molybdenum-on alumina.

The third catalyst having activity for the isomerization of xylene is preferably, an acidic molecular sieve which is characterized by a constraint index in the approximate range of about 1 to about 12. Preferred molecular sieves are borosilicate molecular sieves or ZSM-type zeolite molecular sieves. The molecular sieve used is preferably dispersed on alumina, silica or another suitable matrix. In one embodiment of the invention, the xylene isomerization catalyst may contain a hydrogenation metal selected from metals of groups VI and VIII of the Periodic Table of Elements.

DETAILED DESCRIPTION OF THE INVENTION

The present invention provides a novel means for stabilizing the xylene isomerization activity of a dual bed xylene isomerization catalyst system. This invention is useful for isomerizing a feed containing an aromatic $C_8$ mixture of xylenes and ethylbenzene (EB) in which the para xylene content of the xylene-containing portion of the feed is less than the equilibrium content, to produce a product stream of reduced ethylbenzene content and a greater amount of desired para xylene. Para-xylene is an important hydrocarbon feed material for the manufacture of terephthalic acid. In the present invention, a hydrogenation catalyst bed, for example, a molybdenum-on-alumina (Mo/alumina) catalyst bed, is placed between ethylbenzene conversion and xylene isomerization catalyst components. This sandwich bed system provides an improvement over the dual bed system without the sandwich layer and may cut down on down time of a system by lengthening the time between catalyst regenerations. We believe the hydrogenation bed catalyzes the hydrogenation of olefinic compounds, such as ethylene that is generated over the EB conversion catalyst, thereby inhibiting the coking and subsequent rapid deactivation of the xylene isomerization catalyst component. By controlling the loading of hydrogenation metal, and the relative amount of the hydrogenation catalyst, the ethylene can be quantitatively reduced to ethane without any detrimental effect to the overall performance of the dual bed catalyst. For example, this invention imparts sufficient stability to a transalkylation-type dual bed xylene isomerization catalyst to allow it to operate at greater than one (1) year before catalyst regeneration is necessary.

The ethylbenzene conversion catalyst is a catalyst that selectively catalyzes the conversion of ethylbenzene in the feed mixture to another compound or compounds that can easily be removed from the product mixture. For example, within the scope of the invention, ethylbenzene conversion can occur by, but is not limited to, a transalkylation or disproportionation reaction whereby the ethylbenzene is catalytically converted to benzene and diethylbenzene, or an ethyl group from ethylbenzene is transferred to a xylene molecule thereby forming conversion products that are easily removed from the product mixture. Ethylbenzene conversion can also occur by a deethylation reaction, whereby the ethylbenzene is catalytically converted to benzene and a mixture of ethylene and ethane.

In processes for the manufacture of pure para-xylene, the para-xylene is separated from a $C_8$ feed mixture of xylenes and ethylbenzene using standard methods such as crystallization or adsorption. After removal of the para-xylene, the mother liquor or raffinate is recycled and subjected to isomerization to reestablish a near equilibrium mixture of xylenes. In this isomerization, process, meta-xylene and ortho-xylene are converted to para-xylene. However, it is very difficult to separate ethylbenzene from the xylenes prior to recycle using ordinary separation techniques.

If the ethylbenzene is not removed, it accumulates in the process stream to unacceptable levels. Rather than separate ethylbenzene, most processes for preparing pure para-xylene employ a means to convert ethylbenzene to compounds that can be removed by ordinary separation processes, such as, for example, distillation. The ethylbenzene conversion catalysts described herein serve to affect such conversion reactions.

The xylene isomerization catalyst is a catalyst that will catalyze the conversion of one xylene, such as meta-xylene or ortho-xylene, to another xylene, such as para-xylene. In particular, effective xylene isomerization catalysts will isomerize a mixture of xylenes where the xylenes are present in non-equilibrium amounts to a mixture containing, or very nearly containing, the xylenes in equilibrium amounts at the temperature used for the isomerization reaction. For example, a mixture of xylenes containing ortho-xylene, meta-xylene and para-xylene, where the para-xylene is present in less than the equilibrium amount, can be converted by an effective xylene isomerization catalyst to a mixture of xylenes where the ortho-, meta- and para-xylenes are present at or very near their equilibrium amounts.

This invention is a catalyst system suitable for the isomerization of a xylene and conversion of ethylbenzene in a feed containing xylene and ethylbenzene comprising a first catalyst having activity for the conversion of ethylbenzene, a second catalyst having hydrogenation activity, and a third catalyst having activity for the isomerization of a xylene where the second catalyst is located in the system between the first and third catalysts relative to a flow of feed mixture through the catalyst system.

This invention is also a method for converting a feed mixture comprising an aromatic $C_8$ mixture of xylenes and ethylbenzene in which the para-xylene content of the xylene portion of the feed is less than equilibrium to produce a product mixture of reduced ethylbenzene content and a greater amount of para-xylene, which method comprises contacting the feed mixture at conversion conditions with a first catalyst having activity for the conversion of ethylbenzene, with a second catalyst having hydrogenation activity, and with a third catalyst having activity for the isomerization of a xylene, wherein the second catalyst is positioned between the first and third catalysts relative to the flow of the feed mixture through the catalysts.

As stated previously, a dual bed xylene isomerization catalyst consisting of an EB conversion catalyst component and a xylene isomerization component has been found to have unacceptably high deactivation rates for the xylene isomerization catalyst component. The rapid deactivation of the xylene isomerization catalyst component is believed to be caused by the ethylene that is generated over the EB conversion catalyst. In experiments using only the EB conversion catalyst, we found that the $C_2$ component in the gaseous component of the product consists of more than 80% ethylene.

This rapid deactivation problem was solved in the present invention by placing a hydrogenation catalyst bed between the EB conversion catalyst component and the xylene isomerization catalyst, referred to herein as a "sandwich" bed. In an experiment with the EB conversion catalyst and a hydrogenation catalyst bed in the form of a Mo/alumina catalyst bed below it, we demonstrated that the ethylene produced over the EB conversion catalyst was quantitatively hydrogenated to ethane without any detrimental effect to the other components in the product.

For this invention, the method used to measure the ability of catalyst components to isomerize meta-xylenes (mX) and ortho-xylenes (oX) to para-xylene (pX) is as follows. The open literature and some patents have reported para-xylene approaches to equilibrium (PATE) which exceed 100%. PATE is defined as $$PATE=[(pXprod-pXfeed)/(pXequil-pXfeed)] \times 100,$$

where pXprod is the concentration of pX in xylenes in the product, pXfeed is the concentration of pX in xylenes in the feed, and pXequil is the equilibrium concentration in mole percent of para-xylene among the xylene isomers at the reaction temperature as determined using values reported in the open literature. The quantities pXprod and pXfeed refer to the molar percent of para-xylene among the xylene isomers for the reactor effluent and reactor feeds, respectively.

Those skilled in the art will recognize that PATE is the definition of the molar conversion for a first order reversible reaction. Therefore, it is contrary to the art that PATE can exceed 100%. We have determined that pXequil values as reported and used in the open literature are inconsistent with our experimental results. Thus, in our work and for the teaching of this invention, we have replaced "pXequil" with proper values as determined from our laboratory work. When the pXequil term is replaced with our laboratory determined values, which we have denoted as the "proper pXequil", the new quantity is defined as PPATE, so as to differentiate it from the PATE values commonly reported in the open literature. Open literature values of pXequil for operation at temperatures of commercial interest were described by fitting it to the following equation, where TF is the catalyst temperature in degrees Fahrenheit:

$$(pXequil)=(1-(0.595909-0.132*TF/1000+4.83776*(TF*TF)/100000000)-(0.151814+0.158*TF/1000-5.3*(TF*TF)/100000000)).$$

To convert pXequil to our "proper pXequil", the following correction was used:

$$(Proper\ pXequil)=(1.01824+0.00414*(TF-650)/100)*(pXequil).$$

For example, at 700° F., pXequil is 0.23634, and the proper pXequil is 0.24114.

Two primary functions of the catalyst are conversion of ethylbenzene and isomerization of xylenes to produce para-xylene. The percent ethylbenzene conversion (%EBC) is defined as:

$$\%EBC=[(Feed\_EB\_Effluent\_EB)/(Feed\_EB)] \times 100$$

where Feed_EB is the weight percent ethylbenzene in the hydrocarbons fed to the reactor, and Effluent_EB is the weight percent ethylbenzene in the hydrocarbons exiting the reactor.

In the present invention most of the ethylbenzene conversion (EBC) takes place on one catalyst component and most of the xylene isomerization takes place on a different catalyst component while a third hydrogenation catalyst component is inserted between the ethylbenzene conversion catalyst component and the xylene isomerization component. The use of this third catalyst "sandwich" component is highly effective in preventing a relatively rapid decline in catalyst activity. For many commercial catalysts, ethylbenzene conversion in reactors typically ranges between 10% and 60%, and the conversion of meta- and ortho-xylene to para-xylene as measured by the corrected para-xylene approach to equilibrium (PPATE) typically ranges between 90% and 100%. Because PPATE is typically well in excess of ethylbenzene conversion, a more convenient method to compare relative amounts of these two functionalities on catalyst components is to use Reaction Activity Parameters. The xylene isomerization activity (XIA) parameter is defined as XIA_parameter=−In(1−PPATE/100). The ethylbenzene conversion activity (EBA) parameter is defined as EBA_parameter=−%EBC/(100−%EBC) when EBC proceeds primarily via second order reactions such as the transalkylation of two ethylbenzenes to diethylbenzene and benzene, and EBA_parameter=−In(1−EBC/100) when EBC proceeds primarily via first order reactions such as the de-ethylation of ethylbenzene to benzene and ethane/ethylene. Reaction order is determined by standard methods used by those skilled in the art.

Xylene isomerization feeds, processed in accordance with the invention are any aromatic $C_8$ mixture containing ethylbenzene and xylene(s). Generally, such a mixture will have an ethylbenzene content in the approximate range of about 5 to about 60 weight %, an ortho-xylene content in the approximate range of about 0 to about 35 weight %, a meta-xylene content in the approximate range of about 20 to about 95 weight %, and a para-xylene content in the approximate range of about 0 to about 15 weight %. The feed in addition to the above aromatic $C_8$ mixture can contain non-aromatic hydrocarbons, such as paraffins and naphthenes. The paraffins and naphthenes will generally comprise about 0 to about 20 weight % of the feed; generally, the paraffins and naphthenes will comprise $C_8$–$C_{10}$ paraffins and naphthenes.

The catalyst system used in accordance with the invention is multicomponent. The function of the first catalyst component is to effect conversion of ethylbenzene and $C_8$–$C_{10}$ paraffins and naphthenes to byproducts which are easily separated from the $C_8$ aromatics stream. The function of the second component is to hydrogenate olefins such that deactivation of the third component is inhibited. The function of the third catalyst component is to effect isomerization of the xylene components in the feed to thermal equilibrium.

This invention can be used for, but is not limited to, vapor phase isomerization of a mixture of xylenes with a transalkylation-type (i.e., wherein EB is primarily converted via transalkylation to diethylbenzenes) dual bed catalyst for stabilizing the xylene isomerization activity of the xylene isomerization catalyst. The effectiveness of a Mo/alumina hydrogenation catalyst bed used as the hydrogenation bed is evidenced by a comparison of two long term xylene isomerization runs; a run with the dual bed catalyst and a run with the dual bed catalyst containing a Mo/alumina hydrogenation bed between the EB conversion and xylene isomerization components. We refer to this as the "sandwich bed" catalyst. The reaction conditions for the method of this invention are suitably a temperature of about 480° F. (248.8° C.) to about 1000° F. (537.8° C.), preferably about 500° F. (260° C.) to about 850° F. (454.4° C.), and more preferably about 600° F. (315.6° C.) to about 800° F. (426.7° C.); a pressure of about 0 to about 1000 psig, preferably about 50 to about 600 psig, more preferably about 100 to about 400 psig, and most preferably about 150 to about 300 psig; a hydrogen-to-total hydrocarbon mole ratio of from about 0.5:1 to about 10:1, preferably from about 1:1 to about 10:1, more preferably from about 1:1 to about 6:1, and most preferably from about 1:1 to about 3:1. The Weight Hourly Space Velocity (WHSV) may be in the range of from about 0.5 to about 100, preferably about 2 to about 50, more preferably about 3 to about 20, and most preferably about 4 to about 14. Hydrogen is typically included to hydrogenate coke precursors and hence minimize catalyst deactivation.

In the present invention, either or both of the EB conversion and xylene isomerization components may additionally contain a hydrogenation metal. Such hydrogenation metal may include, but is not limited to, one or more of molybdenum, platinum, palladium, rhodium, or ruthenium.

Even where the EB conversion catalyst component and/or the xylene isomerization catalyst component additionally contain a hydrogenation metal, it is expected that a hydrogenation bed, for example, a molybdenum on alumina catalyst, would still hydrogenate olefins not hydrogenated over the first catalyst bed, and therefore reduce the deactivation of the xylene isomerization component, thus extending its useable life. In general, the xylene isomerization reaction is carried out in a fixed bed flow reactor containing the catalyst system described above. In a preferred embodiment the feed is cascaded over the catalyst system disposed in the reactor in three sequential beds, i.e., the EB conversion catalyst bed, the "sandwiched" hydrogenation catalyst bed, and then the xylene isomerization catalyst bed. The conversion process of the invention could also be carried out in separate sequential reactors wherein the feed would first be contacted with the EB conversion catalyst in a reactor, the effluent from there would be contacted with, the "sandwiched" hydrogenation catalyst in a second reactor, and the resulting effluent stream would then be contacted with the xylene isomerization catalyst in a third reactor.

Catalyst components one and three (i.e., the EB conversion and xylene isomerization catalysts, respectively) contain an acidic molecular sieve which is characterized by a constraint index in the approximate range of about 1 to about 12. Molecular sieves having such a constraint index are often grouped as members of the class of molecular sieves referred to as shape selective. Although an MFI-type of molecular sieve was used in the EB conversion and xylene isomerization components of the sandwich bed catalyst in the embodiment of this invention described in the Examples, other types of molecular sieve catalysts can also be used (e.g., ZSM-11, ZSM-12, ZSM-35, ZSM-38 and other similar materials).

The amount of catalysts and the relative amount of catalysts used in the catalyst system and process of this invention are the amounts that provide for the desired ethylbenzene conversion and xylene isomerization at the reaction conditions that are employed.

When a molecular sieve is used as a component of the isomerization or ethylbenzene conversion catalyst, the amount of molecular sieve can be about 1% to about 100% by weight, more preferably about 10 to about 70% by weight, with the remainder preferably being support matrix material such as alumina or silica. Preferably the support material is silica. The weight ratio of ethylbenzene conversion catalyst to isomerization catalyst is suitably about 1:1 to about 6:1. The weight ratio of ethylbenzene catalyst to hydrogenation catalyst is suitably about 1:1 to about 5:1.

It is preferred that the catalyst component used primarily to effect EB conversion should have an XIA_parameter to EBA_parameter ratio of no more than 10, and preferably between 0 and 2. In the examples given below, the XIA_parameter to EBA_parameter ratios are between 0.5 and 1.5. For the component used for xylene isomerization the XIA_parameter to EBA parameter ratio should be greater than 10. In the examples, ratios have ranged between 200 and 500.

Ethylbenzene conversion catalysts suitable for use in the present invention include but are not limited to Al-MFI molecular sieve dispersed on silica and large particle size molecular sieves, particularly a ZSM-5-type of molecular sieve having a particle size of at least about 1 micron, dispersed on silica, alumina, silica/alumina or other suitable support. The support material is preferably silica. Suitable catalysts based on a ZSM-type molecular sieve, for example, ZSM-5 molecular sieves, are described in U.S. Pat. No. Re. 31,782, which is incorporated herein by reference in its entirety. Other methods known to those skilled in the art, for example reaction of or coating with silicones, resulting in an XIA_parameter to EBA_parameter ratio of no more than 10, are also within the scope of the invention.

The hydrogenation catalyst of the present invention contains a hydrogenation metal, such as molybdenum, platinum, palladium, rhodium, ruthenium, nickel, iron, osmium, iridium, tungsten, rhenium, and the like, dispersed on a suitable matrix. Suitable matrix materials include, but are not limited to, alumina and silica. Although a molybdenum-on-alumina catalyst is preferred, other hydrogenation catalysts, for example those comprising platinum, palladium, rhodium, ruthenium, nickel, iron, osmium, iridium, tungsten, rhenium etc., deposited on a suitable support such as alumina or silica may also be used. It is advantageous to avoid hydrogenation catalysts and/or reaction conditions that cause aromatic ring hydrogenation of the xylenes. When molybdenum-on-alumina is used, it is desirable for the level of molybdenum to be about 0.5 to about 10 weight percent, and preferably about 1 to about 5 weight percent.

The following examples will serve to illustrate certain embodiments of the hereindisclosed invention. These examples should not, however, be construed as limiting the scope of the invention as there are many variations which may be made thereon without departing from the spirit of the disclosed invention, as those of skill in the art will recognize.

General Preparative Procedure for Catalyst Components

In the examples described below, the first catalyst bed, i.e., the catalyst used to convert (remove) ethylbenzene in the feed, was prepared using an Al-MFI, large particle size molecular sieve. The molecular sieve was dispersed on silica to form the catalyst used for the examples. The Al-MFI molecular sieve can be prepared as follows:

Sodium aluminate (3.26 g (0.015 moles)) was dissolved in 680.51 g of distilled water. To this solution was added ethylene diamine (74.89 g (1.246 moles)), followed by tetrapropylammonium bromide (38.13 g (0.143 moles)). The mixture was stirred until solids were not present. To this mixture was added silica sol (Nalco 2327, 40% $SiO_2$ in water; 364.69 g; 2.428 moles), and the mixture was stirred for about 30 minutes. To this mixture was added concentrated sulfuric acid (6.37 g) and the mixture stirred for 15 minutes. This mixture was transferred to a Teflon® lined reactor which was then sealed, and the mixture was stirred at 300 rpm for 4 days at 338° F. at autogenous pressure.

The mixture was filtered and washed with 8 liters of distilled water. The solid product was heated for 4 hours at 328° F., heated to 950 ° F. over a 4 hour period, then heated for 12 hours at 950° F. and then cooled over 4 hours to 120° F. to form the calcined molecular sieve.

The calcined molecular sieve was dispersed on silica in accordance with the following procedure. Molecular sieve (15 g) was mixed dry with Cabosil HS-5 silica (10.06 g). Distilled water (51.45 g) was added slowly with stirring. The resulting paste was calcined by heating at 329° F. for 4 hours, heating to 950° F. over a 4 hour period, heating at 950° F. for 4 hours then cooling to 120° F. over 4 hours. The calcined product was ground and sieved to a 10/40 mesh size.

Although the catalyst made from AI-MFI molecular sieve dispersed on silica was used for the examples below as an ethylbenzene conversion catalyst, other types of ethylbenzene conversion catalyst can be used. Suitable catalysts are also described in U.S. Pat. No. Re 31,782 incorporated herein by reference in its entirety. It is preferable that the ethylbenzene conversion catalyst be prepared using large particle size molecular sieves, particularly a ZSM-5-type of molecular sieve, dispersed on silica, alumina, silica/alumina or other suitable support. Preferably the support material is silica. Preferably, the molecular sieve should have a particle size of at least about 1 micron.

The hydrogenation catalyst used for Examples 1 and 2 below was prepared by impregnating gamma alumina with an aqueous solution of ammonium heptamolybdate followed by drying and then calcining in air in the same manner as the AI-MFI molecular sieve described below was calcined.

Although a molybdenum-on-alumina catalyst was used in the examples below, other hydrogenation catalysts are useful such as one or more noble metals, e.g., platinum, palladium, rhodium, ruthenium, etc., deposited on a suitable support such as alumina or silica. It is advantageous to avoid hydrogenation catalysts and/or reaction conditions that cause aromatic ring hydrogenation of the xylenes. When molybdenum-on-alumina is used, it is desirable for the level of molybdenum to be about 1 to about 5 weight percent.

The xylene isomerization catalyst (i.e., third catalyst bed) described in the examples below was prepared using an AMS-1B borosilicate molecular sieve in the hydrogen form. AMS-1B catalyst can be prepared as described in U.S. Pat. No. 5,053,211, incorporated herein by reference in its entirety. The AMS-1B borosilicate molecular sieve was dispersed on Cytec PHF alumina (methods for dispersing sieve on alumina are also described in U.S. Pat. No. 5,053,211) and contained 20 weight percent molecular sieve and 80 weight percent alumina.

Although an AMS- B-type of molecular sieve was used as the xylene isomerization component of the sandwich bed catalyst in the embodiment of this invention described below, other types of xylene isomerization catalysts can be used as well. For example, catalysts based on ZSM-type, for example, ZSM-5-type molecular sieves, such as those, for example, described in U.S. Pat. No. Re. 31,782, which is also incorporated herein by reference. These molecular sieves can be dispersed on alumina, silica or other suitable matrices.

EXAMPLES OF THE INVENTION

Comparative Example A

Dual Bed Catalyst Run—The dual bed catalyst used in this run consisted of 12 g of the EB conversion catalyst (60% large particle AL-MFI sieve/40% silica) placed on top of 3 g of the xylene isomerization catalyst (a 20% borosilicate sieve on alumina) diluted with 3 g of gamma alumina. The reaction conditions were: Temperature=650° F. (343.3° C.), Pressure=200 psig, a Hydrogen-to-Hydrocarbon ($H_2$/HC) mole ratio of 2.0, and a WHSV of 6.0 (based on EB conversion and xylene isomerization catalyst loadings). The run was carried out at a 25% EB conversion level, and the xylene isomerization activity was monitored by calculating the Percent Approach to Para xylene (pX) Equilibrium (PPATE) defined as:

$$PPATE=[(pXprod-pXfeed)/(Proper\ pXequil-pXfeed)]\times 100,$$

where pXprod is the concentration of pX in xylenes in the product, pXfeed is the concentration of pX in xylenes in the feed, and Proper pXequil is the equilibrium concentration in mole percent of para-xylene among the xylene isomers at the reaction temperature. The feed for the xylene isomerization run contained 17.0% ethylbenzene, 46.0% meta-xylene, 21.7% ortho-xylene and 8.7% para-xylene, by weight; the rest was a mixture of benzene, toluene, non-aromatic and $C_9$–$C_{10}$ aromatics.

After 125 days on stream at the above-mentioned reaction conditions, the PPATE of the dual bed catalyst declined from an initial value of 98.5% to 92.0%. This corresponds to an average deactivation rate of 0.05%/day. During this same period, the catalyst did not exhibit any significant decline in its EB conversion activity.

Example 1

Sandwich Bed Catalyst Run—The sandwich bed catalyst used in this run consisted of 12 g of the EB conversion catalyst (60% large particle AL-MFI sieve/40% silica) placed on top of 4 g of 2% Mo/alumina placed on top of 3 g of the xylene isomerization catalyst (a 20% borosilicate sieve-on-alumina) diluted with 3 g of alumina. As in the dual bed catalyst run, the EB conversion was maintained at 25% and the PPATE was monitored. The reaction conditions for this run were: Temperature=655° F. (346.1° C.), Pressure=260 psig, $H_2$/HC mole ratio=2.0 at a WHSV of 6.0 (based on the EB conversion and xylene isomerization catalyst loadings).

After 125 days on stream, PPATE of the sandwich bed catalyst declined from an initial value of 99% to only 98%. This corresponds to an average deactivation rate of 0.008%/day which is a significant and unexpected improvement over the corresponding rate of 0.05%/day from the dual bed catalyst (a 6-fold reduction in deactivation rate). A comparison of performance of the dual bed and sandwich bed catalysts is shown in FIG. 1.

Example 2

Sandwich Bed Catalyst Run—The scope of this invention is further illustrated by another long term run conducted with a sandwich bed catalyst under lower $H_2$/HC mole ratio conditions. The reaction conditions for this run were: Temperature=655–672° F. (346.1° C.–354.4° C.), Pressure=265 psig, $H_2$/HC mole ratio=1.4, at a WHSV of 6.0 (based on the loading of the EB conversion and xylene isomerization catalysts). The sandwich bed catalyst loading was the same as described in the sandwich bed catalyst run of Example 1.

The sandwich bed catalyst in this run was evaluated for a period of 513 days on stream. During this period, the xylene isomerization activity declined from an initial PPATE of 99.4% to 96.4%. This corresponds to an average deactivation rate of 0.006%/day, which is consistent with the rate that was observed in the sandwich bed run of Example 1.

What is claimed is:

1. A process for converting a feed mixture comprising an aromatic $C_8$ mixture of xylenes and ethylbenzene in which the para-xylene content of the xylene portion of the feed is less than equilibrium to produce a product mixture of reduced ethylbenzene content and a greater amount of para-xylene, which method comprises contacting the feed mixture at conversion conditions through a first catalyst having activity for the conversion of ethylbenzene, through a second catalyst having hydrogenation activity, and through a third catalyst having activity for the isomerization of a xylene, wherein the second catalyst is positioned between the first and third catalysts relative to the flow of the feed mixture through the catalysts.

2. A process according to claim 1 for isomerizing a feed containing an aromatic $C_8$ mixture of ethylbenzene and xylene in which the para-xylene is less than at thermal equilibrium which comprises contacting the feed under isomerization conditions with a three-component catalyst system including component (1), component (2), and component (3) wherein component (1) comprises a catalyst having activity for the conversion of ethylbenzene, component (2) comprises a catalyst having hydrogenation activity, and component (3) comprises a catalyst having activity for the isomerization of a xylene and wherein component (2) is located in the system between component (1) and component (3) relative to a flow of the ethylbenzene/xylene feed through the catalyst system.

3. The process of claim 2 wherein the feed is contacted with component (1) of the catalyst system before the feed is contacted with component (2) of the catalyst system.

4. The process of claim 2 wherein the catalyst system is a fixed bed catalyst system.

5. The process of claim 4 wherein component (1), component (2), and component (3) are in sequential beds in the fixed bed catalyst system.

6. A process according to claim 2 for isomerizing a feed containing an aromatic $C_8$ mixture of ethylbenzene and xylene in which the para-xylene is less than at thermal equilibrium which comprises contacting the feed under-isomerization-conditions at a temperature of from about 480° F. to about 1000° F., a pressure of about 0 to about 1000 psig, a hydrogen-to-total hydrocarbon mole ratio of from about 0.5:1 to abut 10:1, and a weight hourly space velocity (WHSV)of from about 0.5 to about 20, with a three-component catalyst system including component (1), component (2), and component (3) wherein component (1) comprises a catalyst having activity for the conversion of ethylbenzene, component (2) comprises a catalyst having hydrogenation activity, and component (3) comprises a catalyst having activity for the isomerization of a xylene and wherein component (2) is located in the system between component (1) and component (3) relative to a flow of the ethylbenzene/xylene feed through the catalyst system.

7. The process of claim 1 wherein the catalyst having activity for the conversion of ethylbenzene is a molecular sieve having a particle size of at least about 1 micron.

8. The process of claim 7 wherein the catalyst having activity for the conversion of ethylbenzene is dispersed on a support selected from silica, alumina, and silica-alumina.

9. The process of claim 1 wherein the catalyst having activity for the conversion of ethylbenzene is an Al-MFI molecular sieve or a ZSM-5-type molecular sieve dispersed on a support selected from silica, alumina and silica-alumina.

10. The process of claim 9 wherein the catalyst having activity for the conversion of ethylbenzene additionally contains a hydrogenation metal.

11. The process of claim 1 wherein the catalyst having hydrogenation activity comprises a hydrogenation metal on a matrix.

12. The process of claim 11 wherein the catalyst having hydrogenation activity comprises a hydrogenation metal selected from molybdenum, platinum, palladium, rhodium, ruthenium, nickel, iron, osmium, iridium, tungsten, and rhenium dispersed on a matrix selected from alumina and silica.

13. The process of claim 12 wherein the catalyst having hydrogenation activity comprises a molybdenum-on-alumina catalyst.

14. The process of claim 13 wherein the level of molybdenum in the catalyst is about 0.5 to about 10 weight percent.

15. The process of claim 1 wherein the catalyst having activity for the isomerization of xylene is a borosilicate molecular sieve or zeolite molecular sieve on a support selected from silica, alumina, and silica-alumina.

16. The process of claim 1 wherein the catalyst having activity for the isomerization of xylene is an AMS-1B-type molecular sieve or a ZSM-5-type molecular sieve dispersed on a support selected from silica, alumina and silica-alumina.

17. The process of claim 16 wherein the catalyst having activity for the isomerization of xylene additionally contains a hydrogenation metal.

18. The process of claim 1, wherein the catalyst system is a fixed bed catalyst system.

19. The process of claim 18, wherein the three catalysts are in sequential beds in the fixed bed catalyst system.

20. The process of claim 19, wherein the three catalysts are in sequential reactors.

* * * * *